United States Patent [19]
Ernryd et al.

[11] Patent Number: 4,591,437
[45] Date of Patent: May 27, 1986

[54] APPARATUS FOR SEPARATING SOLID PARTICLES FROM A LIQUID

[75] Inventors: Leif W. Ernryd, Jämjöslätt; Vlastimil Carbol; Paul Carbol, both of Växjö, all of Sweden

[73] Assignee: Leif Ernryd AB, Jämjöslätt, Sweden

[21] Appl. No.: 499,890

[22] Filed: Jun. 1, 1983

[30] Foreign Application Priority Data

Jun. 4, 1982 [SE] Sweden ................. 8203454

[51] Int. Cl.³ .......................................... B01D 23/10
[52] U.S. Cl. ................... 210/265; 210/266; 210/284
[58] Field of Search ........... 210/265, 266, 290, 500.1, 210/503, 505, 284

[56] References Cited

U.S. PATENT DOCUMENTS

| 1,398,285 | 11/1921 | Tanner | 210/266 |
| 1,838,263 | 12/1931 | Kelley | 210/265 |
| 1,992,420 | 2/1935 | Gleason et al. | 210/134 |
| 3,382,983 | 5/1968 | Stewart | 210/266 |
| 3,471,025 | 10/1969 | Dobson | 210/290 |

FOREIGN PATENT DOCUMENTS 1054070  4/1959  Fed. Rep. of Germany .

Primary Examiner—Ivars Cintins
Attorney, Agent, or Firm—Shapiro and Shapiro

[57] ABSTRACT

Apparatus for separating solid particles, such as amalgam waste from the waste water from dentists' surgical units, employs at least one filter body through which the liquid flows and which consists of a filter medium enclosed between two perforated walls, and at least one sedimentation zone. The filter medium consists of balls of alumina having a diameter of 0.05–15 mm and a density such that the balls float in or are carried along by the liquid flowing through the filter body. The balls, which do not fill out the entire volume between the perforated walls (although they fill out the cross-sectional area of the filter body), rub against each other in the flowing liquid, so that the filter body is self-cleaning.

10 Claims, 3 Drawing Figures

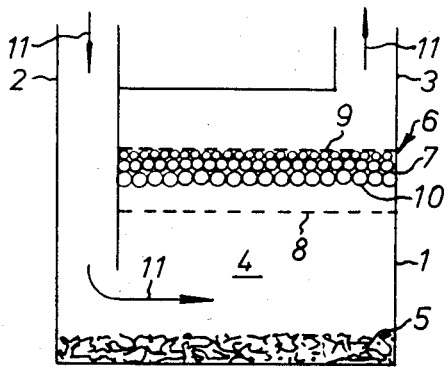
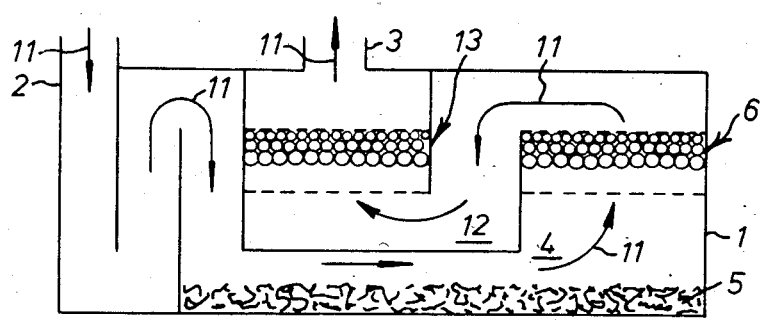
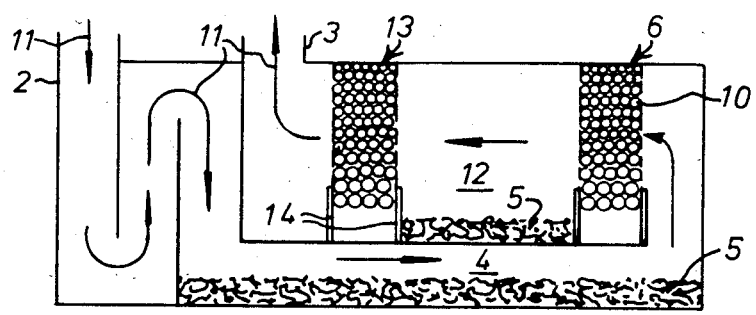

APPARATUS FOR SEPARATING SOLID PARTICLES FROM A LIQUID

The present invention relates to an apparatus for separating solid particles from a liquid, more particularly for separating amalgam waste from the waste water in dentists' surgical units.

Mercury and mercury-containing products constitute a serious environmental hazard, and it is therefore endeavoured to eliminate as far as possible the discharge of such substances.

A major source of mercury emission is the dental health service, such as dental surgeries, odontological institutes, dental laboratories etc. which for fillings and the like consume large quantities of mercury in the form of amalgam and other alloys of varying composition. It has been estimated that as much as about 20% of the consumed amount of amalgam is discharged in the form of solid residues with the waste water from dental surgeries. It is therefore desirable from an environmental point of view of recover the amalgam waste from dental activities and to eliminate as far as possible the discharge of amalgam and other waste from such activities.

To this end, Swedish authorities have decided that, from July 1, 1980, all new dental equipment must be provided with separation facilities affording a 95% purification degree in respect of amalgam, and furthermore all dental equipment, new as well as old, must be provided with such separation facilities by Jan. 1, 1985, at the latest. To check that the separation facilities satisfy the requirement for a 95% purification degree, standard tests are conducted for separation facilities for mercury-containing waste in the waste water from dentists' surgical units. The particulate amalgam waste which is to be separated by the test, consists of amalgam composed of 51% by weight mercury, 32% by weight silver, 13% by weight tin, 8% by weight copper and 1% by weight zinc. In order to simulate practical conditions as far as possible, the amalgam is comminuted and screened to a particle size such that 10% are 0.020–0.044 mm, 15% are 0.044–0.350 mm, 25% are 0.350–1 mm, and 50% are 1–2 mm. The amalgam waste is suspended in water in an amount of 10 g/liter and is supplied to the separation apparatus in a flow of 100 ml/min., together with water in such an amount that the total flow corresponds to the maximum flow of the separation apparatus (normally about 10–15 l/min.).

Separation apparatus for dentists' surgical units are previously known, but suffer from several disadvantages. Thus, apparatus of the vacuum type are available in which the waste water is sucked by vacuum into a cyclone separator in which particulate pollutants, such as amalgam residues, are separated and collected in a collection cup. Apparatus of this type must be integrated with the electrical control system of the dentist's surgical unit, and the great variety of differently designed surgical units makes the installation of this type of apparatus complicated and expensive. Another type of apparatus uses a power-driven rotor by which the waste water is flung outwardly, the waste particles being collected and the water discharged. Although this is, per se, a simpler construction, it suffers from the disadvantage that the fouling caused by the infected waste water may cause unbalance of the rotor, with the ensuing risk of breakdown. Finally, a third type of apparatus operates by promoting sedimentation of the particles in the waste water which is conducted through a multiplicity of small transverse passages. Also in this type of apparatus, fouling and ensuing difficulties are encountered, and furthermore it is difficult to remove the collected particles.

In prior art separation apparatus it is not possible to avoid discharge of infected and amalgam-containing water during handling of the collection cups. It is also difficult to train and motivate the personnel of dental surgeries for this type of work. On the whole, it must be regarded as improper to expose infected waste water in this type of environment where patients are being treated and operated on. However, before the present invention was made, no other alternative existed.

The present invention has for its object to obviate the disadvantages of prior art technique and to provide a separation apparatus which effectively collects solid particles, such as amalgam waste, and which satisfies the above-mentioned requirement for a 95% degree of purification and which, furthermore, is easily handled and requires little supervision.

To this end, the apparatus according to the invention has been designed as a combined sedimentation and filtration device in which the filter is of a special type and comprises a filter body in which the filter medium is in the form of balls having a density such that the balls either float in or are carried along by the liquid flowing through the filter body.

An essential difference between the present invention and prior art separation apparatus for dentists' surgical units is that the apparatus according to the invention is adapted to be replaced in its entirety after a predetermined period of operation which, depending upon different factors, is intended to lie between 4 and 12 months.

The characteristic features of the invention will appear from the appended claims.

The following is a description of the separation of amalgam residues and other particulate waste in the dental health service, using the separation apparatus according to the invention.

The separation apparatus according to the invention generally comprises a closed separation container having an inlet for liquid containing solid particles and an outlet for purified liquid from which solid particles have been separated. Furthermore, there is provided within the separation container at least one sedimentation zone through which the liquid is conducted while particles having a density higher than that of the liquid are allowed to settle. To retain settled particles and prevent the particles from being carried along by the liquid flow, the sedimentation zone preferably is provided at its bottom with a layer of absorption material. As long as this layer is capable of absorbing and retaining the settled material, the composition of the absorption material is not critical. Preferably, however, it is a fibrous material, primarily an inorganic fibrous material, such as glass fibres, mineral wool fibres or the like. The fibre diameter preferably is about 1–20 μm. It is especially preferred that the absorption material consists of fibres of alumina. When the settled waste material consists of amalgam residues, it is also possible to use, as the absorption material, mercury in the form of a layer on the bottom of the sedimentation zone, but this possibility is less preferred, primarily for environmental reasons, but also because of the cost involved.

Besides one or more sedimentation zones, the separation container according to the invention also comprises at least one filter body of special construction. Generally, the filter body according to the invention is a ball-shaped filter medium which is enclosed between two perforated walls, such as wire nettings or apertured panels, whereas the remaining boundary walls of the filter body are impermeable to liquid. The main object of the perforated walls is to retain the ball-shaped filter medium in the filter body, but they also serve to distribute, with a reasonable degree of uniformity, the liquid flow through the filter body. The throughflow area of the filter body may be of any suitable design, such as rectangular or square-shaped, but a circular shape is especially preferred. The ball-shaped filter medium within the filter body consists of a material capable of adsorbing on its surface the particulate material of the liquid. Examples of such materials for the filter medium are organic polymeric materials, such as polyethylene, polypropylene, polyvinyl chloride etc., and inorganic materials such as quartz and glass. As is the case with the absorption material in the sedimentation zone, the filter medium should preferably consist of alumina. Not only is this material inert and resistant in the environment here concerned; it is also wear resistant and durable. Furthermore, it is possible to use a combination of balls and different materials, such as plastic and alumina, the plastic balls also having a lubricating effect and facilitating the rubbing action of the balls against one another. The ball size is selected within the range 0.05–15 mm, preferably so that the filter body contains balls of different sizes, both greater and smaller, within the range indicated. The amount of the balls within the filter body should be such that at least the cross-sectional area of the filter body through which the liquid passes, is filled out by the balls, while at the same time the total volume taken up by the balls should be less than the total volume of the filter body. This means that normally the filter body is not completely filled with the balls. Furthermore, the density of the filter medium balls should be such that it lies at or below the density of the liquid. More particularly, preferably all balls or at least the major part thereof should have a density below that of the liquid, while a minor part of the balls may have a density exceeding that of the liquid. However, the density of the balls should not exceed the density of the liquid by more than about 25%.

Basically, the function of the filter body according to the present invention is as follows. When the liquid flow is shut down, the balls having a density higher than that of the liquid lie on the bottom of the filter body, whereas the balls having a density below that of the liquid because of their buoyancy are in contact with the upper part of the filter body. When the flow of particle-contaminated liquid is initiated, all filter medium balls are collected to engage the outlet end of the filter body, on the one hand because of their buoyancy and, on the other hand, because they are carried along by the liquid flow. Due to the liquid flow, and because the filter body is not completely filled with balls, the balls will be set in rubbing motion relative to one another. In this manner, the pollutant particles adsorbed on the surface of the balls will be rubbed off the surface, and when the liquid flow is interrupted, the waste particles can settle and collect on the bottom of the separation container.

The above-described function implies that the filter body according to the invention is self-cleaning so that it is not blocked by separated material, such as amalgam waste, or blocked through fouling, which is a common problem in dentists' surgical units because the waste water is contaminated by bacteria.

As has been mentioned above, the filter medium balls according to the present invention preferably consist of alumina which normally has a density of about 3.4 g/cm$^3$. However, a suitable density of about 0.8–0.9 g/cm$^3$ is obtainable by making the balls hollow. A suitable density for balls heavier than the liquid (water) is about 1.1 g/cm$^3$. In the present invention, the density of the alumina balls thus generally lies at 0.8–3.4 g/cm$^3$, preferably at 0.8–1.1 g/cm$^3$ and, most preferred, at 0.8–0.9 g/cm$^3$.

To facilitate understanding of the invention, the following illustrative and nonrestrictive description is given, reference being made to the accompanying drawings in which FIG. 1 is a diagrammatic cross-sectional view of an apparatus according to the invention comprising a filter body;

FIG. 2 illustrates another embodiment of the invention comprising two filter bodies with vertical throughflow; and FIG. 3 illustrates a third embodiment of the invention comprising two filter bodies with horizontal throughflow.

The apparatus according to FIG. 1 comprises a closed separation container 1 having an inlet 2 for waste water contaminated by amalgam waste particles, and an outlet 3 for purified waste water which is free from amalgam particles. In the drawings, the inlet and the outlet are shown schematically, but to make them readily adaptable to the dentist's surgical unit, they are preferably made vertically movable and rotatable. The inlet 2 opens into a sedimentation zone 4 in which the amalgam particles are allowed to settle towards the container bottom which may be provided with an absorption material 5, such as alumina wool, as is shown in FIG. 1. The waste water then continues upwards through the filter body 6 which is circumferentially surrounded by a liquid-impermeable, preferably circular side wall 7 and which, in the direction of flow of the waste water, is bounded by two perforated walls 8 and 9 on either side of the filter body. As has been mentioned before, these perforated walls preferably are made of wire netting. Disposed within the filter body is a filter medium in the form of balls 10. When the waste water flows through the separation container, as is shown by the arrows 11, the filter medium balls, due to the liquid flow and the buoyancy of the balls, collect against the upper wire netting of the filter body. The layer of balls 10 constitutes an effective filter preventing the passage of amalgam particles in the waste water and permitting only purified waste water free from amalgam particles to pass. When the liquid flow through the separation container is interrupted, also the amalgam particles detached from the balls by the rubbing motion of the balls relative to one another, will settle towards the bottom of the separation container which, in this instance, constitutes the sedimentation zone 4.

Basically, the apparatus shown in FIG. 2 operates in the same manner as the apparatus according to FIG. 1, and for the sake of simplicity, like components are identified by the same reference numerals as in FIG. 1. The apparatus according to FIG. 2 constitutes a further improvement on the apparatus according to FIG. 1 and distinguishes therefrom in that the liquid at the beginning of the sedimentation zone 4 is conducted in a meandering path to further improve the separation of coarse waste particles, such as amalgam, tooth rests and the like. As in FIG. 1, the waste water is conducted from the sedimentation zone 4 in a vertical flow through a filter body 6. In the apparatus according to FIG. 2, further purification is accomplished by passing the waste water through a second sedimentation zone 12 which in FIG. 2 has no absorption material but which, like the sedimentation zone 4, may of course be provided with such absorption material. After the sedimentation zone 12, the waste water flows vertically upwards through a second filter body 13 of the same construction as the first filter body 6, and then the purified waste water is discharged through the outlet 3.

FIG. 3 illustrates an alternative embodiment of the invention, in which the filter bodies are positioned vertically and the waste water flows horizontally through the filter bodies. In other respects, the embodiment according to FIG. 3 substantially corresponds to the one shown in FIG. 2, and like details have, of course, been given the same reference numerals. As in FIG. 2, the waste water enters the apparatus according to FIG. 3 through the inlet 2 and then flows in a meandering path and over a layer of absorption material 5 in the sedimentation zone 4, whereupon the liquid passes through a first, vertically positioned filter body 6. Because the filter body is not completely filled with filter medium balls 10, the filter body 6 in FIG. 3 is provided with baffles 14 covering the space of the filter body not filled with filter medium balls, thereby to force the waste water to flow through that part of the filter body which is filled with filter balls. After the first filter body 6, the waste water passes through a second sedimentation zone 12 which, in this instance, is shown with a layer of absorption material 5. The waste water then passes a second filter body 13 which in FIG. 3 is formed in the same manner as the first filter body 6 but which may also be formed differently, for instance as a conventional filter body of the sedimentation type. The relative order of such a conventional filter body and the filter body according to the invention may also be reversed. Finally, the waste water liquid containing no solid particles is discharged through the outlet 3.

The invention has been shown and described above with reference to certain preferred embodiments, but it will be appreciated that variations and modifications are possible without departing from the scope of the invention. For instance, the apparatus may be a combination of the embodiments shown in FIGS. 2 and 3, in that it incorporates filter bodies for both vertical and horizontal throughflow of the liquid to be purified, a combination which in some cases has given excellent results. Furthermore, the apparatus may comprise, in addition to the specific filter body according to the invention, also filter bodies of conventional type, as has been indicated above.

What we claim and desire to secure by Letters Patent is:

1. An apparatus for separating solid particles, such as amalgam waste, from the waste water from dentists' surgical units, said apparatus comprising a separation container (1) having an inlet (2) for liquid containing solid particles and an outlet (3) for purified liquid from which solid particles have been separated, at least one filter body (6, 13) through which the liquid flows and which consists of a filter medium enclosed between two perforated walls (8, 9), and at least one sedimentation zone (4, 12) for the sedimentation of solid particles, characterised in that the filter medium of at least one of said filter bodies consists of balls (10) of alumina having a diameter of 0.05-15 mm, said balls having a density such that they either float in or are carried along by the liquid flowing through the filter body (6, 13), and said balls (10) being present in such an amount that they take up a total volume which is sufficiently less than the total volume of the space between said perforated walls (6, 13) as to leave a region of said space devoid of said filter medium, and said balls (10) filling out at least the cross-sectional area of the filter body (6, 13) through which the liquid flows.

2. An apparatus as claimed in claim 1, characterised in that the balls (10) are hollow and have a density of 0.8-3.4 g/cm$^3$.

3. An apparatus as claimed in claim 2, characterised in that the balls (10) have a density of 0.8-1.1 g/cm$^3$.

4. An apparatus as claimed in claim 3, characterised in that the balls (10) have a density of 0.8-0.9 g/cm$^3$.

5. An apparatus as claimed in claim 1, characterised in that it has a sedimentation zone (4) between the inlet and the filter body or bodies (6).

6. An apparatus as claimed in claim 1, characterised in that it has two filter bodies (6, 13) with an intermediate sedimentation zone (12).

7. An apparatus as claimed in claim 1, characterised in that at least one sedimentation zone (4, 12) comprises a layer of absorption material (5).

8. An apparatus as claimed in claim 7, characterised in that the absorption material (5) consists of alumina fibres.

9. An apparatus as claimed in claim 8, characterised in that the fibres have a diameter of 1-20 μm.

10. An apparatus as claimed in claim 1, characterised in that the perforated walls are horizontal and a sedimentation zone (4, 12) is positioned beneath said at least one filter body (6, 13) to receive solid particles which are rubbed off said balls.

* * * * *